United States Patent [19]
Jautelat et al.

[11] 4,327,025
[45] Apr. 27, 1982

[54] PREPARATION OF STYRYL-CYCLOPROPANE-CARBOXYLIC ACID ESTERS AND INTERMEDIATE THEREFOR

[75] Inventors: Manfred Jautelat, Burscheid; Dieter Arlt, Cologne; Reinhard Lantzsch, Leverkusen; Rainer Fuchs, Wuppertal; Hans-Jochem Riebel, Wuppertal; Rolf Schröder, Wuppertal; Horst Harnisch, Much, all of Fed. Rep. of Germany

[73] Assignee: Bayer Aktiengesellschaft, Leverkusen, Fed. Rep. of Germany

[21] Appl. No.: 137,685

[22] Filed: Apr. 7, 1980

[30] Foreign Application Priority Data

Apr. 23, 1979 [DE] Fed. Rep. of Germany ....... 2916321

[51] Int. Cl.³ ................ C07D 325/00; C07D 317/44; C07C 121/60; C07C 69/76
[52] U.S. Cl. .......................... 260/338; 260/340.5 R; 260/343.6; 260/348.49; 260/465 D; 260/951; 560/17; 560/62; 568/442; 568/655
[58] Field of Search .................................. 560/17, 62; 260/340.5 R, 465 D, 338

[56] References Cited

U.S. PATENT DOCUMENTS

| | | | |
|---|---|---|---|
| 3,077,496 | 2/1963 | Julia . | |
| 3,120,551 | 2/1964 | Goldschmidt | 260/544 D |
| 3,213,072 | 10/1965 | Hoffenberg et al. | 560/62 |
| 3,652,652 | 3/1972 | Julia . | |
| 4,016,179 | 4/1977 | Fujimoto et al. | 260/465 D |
| 4,161,535 | 7/1979 | Meyer et al. | 260/544 D |
| 4,199,595 | 4/1980 | Berkelhamer et al. | 260/544 S |
| 4,201,787 | 5/1980 | Katsuda et al. | 560/62 |
| 4,204,071 | 5/1980 | Anderson et al. | 260/465 D |
| 4,227,015 | 10/1980 | Collins | 560/62 |

FOREIGN PATENT DOCUMENTS

| | | |
|---|---|---|
| 283320 | 8/1970 | Austria . |
| 2539895 | 3/1976 | Fed. Rep. of Germany . |
| 2706184 | 8/1977 | Fed. Rep. of Germany . |
| 2738150 | 3/1978 | Fed. Rep. of Germany . |
| 2740849 | 3/1979 | Fed. Rep. of Germany . |
| 2827101 | 1/1980 | Fed. Rep. of Germany . |
| 54-34723 | 10/1979 | Japan ..................... 560/62 |
| 813539 | 5/1959 | United Kingdom . |

OTHER PUBLICATIONS

Roedig et al., Chem. Ber. 111, 860–868 (1978).
Kondo et al., Tetrahedron Letters, No. 48, pp. 4359–4362 (1976).
H. Kroper: Lactone.

*Primary Examiner*—Ethel G. Love
*Attorney, Agent, or Firm*—Sprung, Felfe, Horn, Lynch & Kramer

[57] ABSTRACT

A process for the preparation of a styrylcyclopropane-1-carboxylic acid ester of the formula

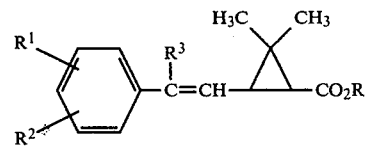

in which
R is $C_{1-4}$-alkyl or an alcohol radical customary in pyrethroids,
$R^1$ is alkoxy or alkylthio, either of which may be optionally substituted by halogen,
$R^2$ is hydrogen or alkoxy, or
$R^1$ and $R^2$ together are optionally halogen-substituted alkylenedioxy, and
$R^3$ is hydrogen or chlorine, comprising reacting an ester of the formula

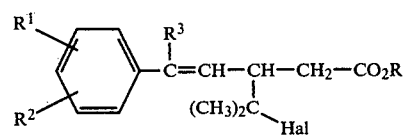

in which
Hal is chlorine or bromine,
with a base.

The compounds are insecticidally active. Numerous syntheses of the starting materials, some involving new intermediates, are also shown.

1 Claim, No Drawings

PREPARATION OF STYRYL-CYCLOPROPANE-CARBOXYLIC ACID ESTERS AND INTERMEDIATE THEREFOR

The present invention relates to an unobvious process for the preparation of styryl-cyclopropane-carboxylic acid esters, and intermediate products for carrying out this process and their preparation.

It has already been disclosed that certain esters of 3-styryl-2,2-dimethylcyclopropanecarboxylic acids have insecticidal properties (German Offenlegungsschrift (German Published Specification) 2,738,150). However, no economical industrial-scale synthesis for carboxylic acids of this type is yet known.

The linking of the C—C double bond of the styryl group is effected by a Wittig reaction, in which butyllithium is used as the base and which must be carried out at $-78°$ C. under an inert gas. This synthesis route is thus not practicable for an industrial preparation.

Furthermore, no synthesis is known which can be used for the preparation on a relatively large scale of the 2,2-dimethyl-3-formyl-1-carboxylic acid esters which are required as starting materials.

1. The present invention now provides a process for the preparation of a styryl-cyclopropane-carboxylic acid ester of the general formula

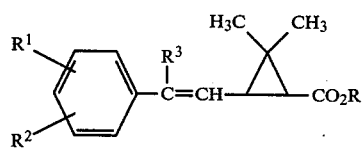

in which
R represents an alcohol radical customary in pyrethroids or $C_{1-4}$-alkyl,
$R^1$ represents alkoxy or alkylthio, either of which may be optionally substituted by halogen,
$R^2$ represents hydrogen or alkoxy or
$R^1$ and $R^2$ together represent optionally halogen-substituted alkylenedioxy and
$R^3$ represents hydrogen or chlorine,
in which a compound of the general formula

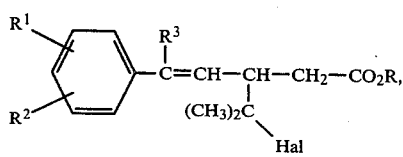

in which
R, $R^1$, $R^2$ and $R^3$ have the meanings indicated above and
Hal represents chlorine or bromine,
is reacted with an optionally aqueous base, if appropriate in the presence of a diluent and in the presence of a phase-transfer catalyst.

2. It has also been found that the compounds of the formula (I) are formed when bases which are not too strong are used and when the reaction is carried out in the presence of a phase transfer catalyst.

3. The new compounds of the general formula (II) in which
R, $R^1$, $R^2$, $R^3$ and Hal have the meanings indicated above, have also been found.

4. A process has also been found for the preparation of a compound of the general formula (II), characterized in that a compound of the general formula

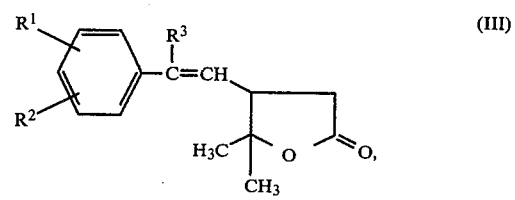

in which
$R^1$, $R^2$ and $R^3$ have the meanings indicated hereinabove,
is reacted with a halogenating agent and, at the same time or successively, with an alcohol of the general formula

R—OH  (IV), in which
R has the meaning indicated under 1. (above),
if appropriate in the presence of a diluent and if appropriate in the presence of a gaseous hydrogen halide.

5. The new compounds of the formula (III) in which
$R^1$, $R^2$ and $R^3$ have the meanings indicated under 1. (above),
have also been found.

6. A process has also been found for the preparation of a compound of the formula (III), characterized in that
(a) a compound of the general formula

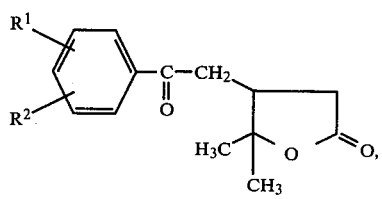

in which
$R^1$ and $R^2$ have the meanings indicated above,
is reacted with phosphorus pentachloride, or
(b) a compound of the general formula

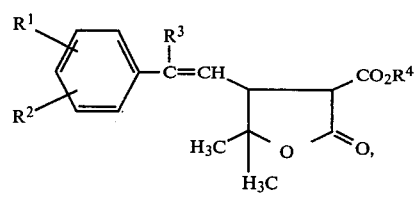

in which
$R^1$, $R^2$ and $R^3$ have the meanings indicated hereinabove and
$R^4$ denotes $C_{1-4}$-alkyl,
is decarboxylated or saponified and decarboxylated, or
(c) a compound of the formula (V) above,
in which
$R^1$ and $R^2$ have the meanings indicated above,
is reduced and water is split off from the product.

7. The new compounds of the formula (V)
in which
$R^1$ and $R^2$ have the meanings indicated hereinabove, have also been found.
8. The new compounds of the formula (VI)
in which
$R^1$, $R^2$, $R^3$ and $R^4$ have the meanings indicated hereinabove,
have also been found.
9. A process has also been found for the preparation of a compound of the general formula (VI), characterized in that a compound of the general formula

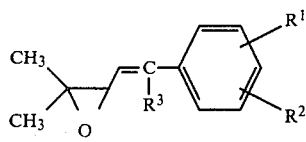 (VII)

in which
$R^1$, $R^2$ and $R^3$ have the meanings indicated hereinabove,
is reacted with a malonic ester of the general formula

 (VIII), in which
$R^4$ denotes $C_{1-4}$-alkyl,
in the presence of a base and, if appropriate, in the presence of a diluent.
10. It has also been found that the compounds of the formula (VI) are preferably obtained by process 9 if the reaction is carried out below 50° C.
11. The new compounds of the formula (VII) in which $R^1$, $R^2$ and $R^3$ have the meanings indicated hereinabove,
have also been found.
12. A process has also been found for the preparation of a compound of the general formula (VII), characterized in that a compound of the general formula

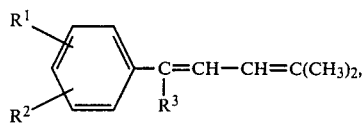 (IX)

in which
$R^1$, $R^2$ and $R^3$ have the meanings indicated above,
is oxidized.
13. The new compounds of the formula (IX) in which $R^1$, $R^2$ and $R^3$ have the meanings indicated hereinabove,
have also been found.
14. A process has also been found for the preparation of a compound (IX), characterized in that
(a) a compound of the general formula

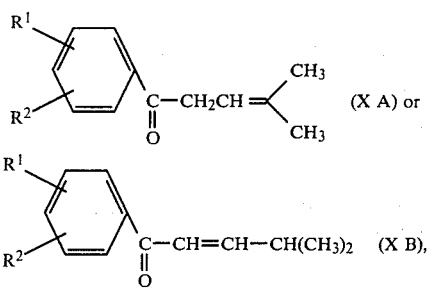 (X A) or (X B)

in which formulae
$R^1$ and $R^2$ have the meanings indicated hereinabove,
or a mixture thereof, is reacted with phosphorus pentachloride and the product is then reacted with a base,
or (b) a compound of the general formula

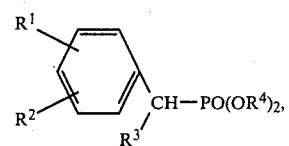 (XI)

in which
$R^1$, $R^2$, $R^3$ and $R^4$ have the meanings indicated hereinabove,
is reacted with dimethylacrolein, of the formula $(CH_3)_2C=CH-CHO$ (XII), or (c) a compound of the general formula

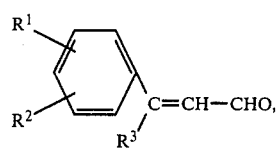 (XVII)

in which
$R^1$, $R^2$ and $R^3$ have the meanings indicated hereinabove,
is reacted with the compound of the formula

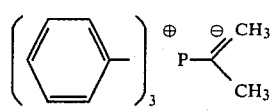 (XVIII)

or (d) a compound of the formula (XVII) is reacted with isopropyl-magnesium chloride, of the formula $(i-C_3H_7-MgCl)$ (XIX).

15. A process has also been found for the preparation of a compound of the general formula

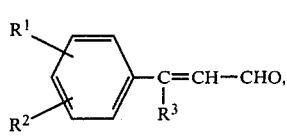 (XVII)

in which
$R^1$ and $R^2$ have the meanings indicated hereinabove and
$R^3$ represents chlorine,
characterized in that an acetophenone of the general formula

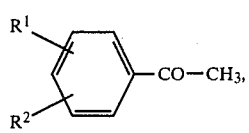 (XVI)

in which $R^1$ and $R^2$ have the meanings indicated hereinabove, is reacted with $POCl_3$ and dimethylformamide, without the addition of a diluent, and the reaction product is isolated by hydrolysis, without working up by distillation.

16. A process has also been found for the preparation of certain compounds of the general formula

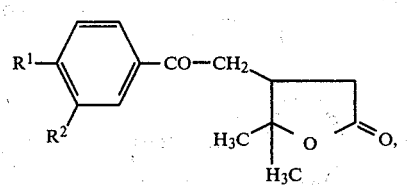  (V)

in which $R^1$ and $R^2$ have the meanings indicated above, but may not be substituted by halogen, which is characterized in that the compound of the formula

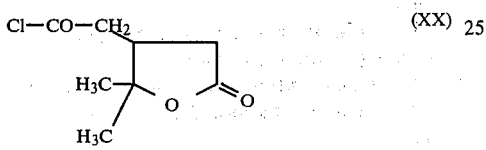  (XX)

is reacted with a compound of the general formula

  (XXI)

in which $R^1$ and $R^2$ have the meaning indicated under 16, in the presence of a Friedel-Crafts catalyst and if appropriate in the presence of a diluent.

17. The compound of the formula (XX) is obtained by a process in which the compound of the formula

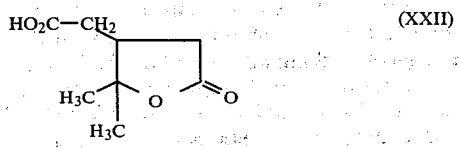  (XXII)

is reacted with a chlorinating agent.

The styrylcyclopropanecarboxylic acid esters of the formula (I) which can be prepared by process 1 (above) have an insecticidal and acaricidal action.

If 5-(4'-methoxyphenyl)-5-chloro-3-(1'-chloro-1'-methyl)-ethyl-pent-4-enoic acid ethyl ester is used as the starting substance in process 1 (above), the course of the reaction can be represented by the following equation:

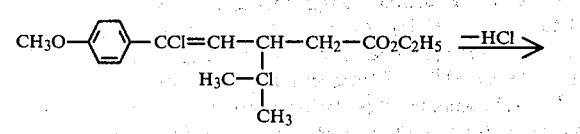

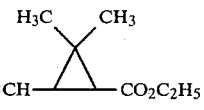

The general formula (II),
in which, preferably,
$R^1$ represents $C_1$–$C_4$-alkoxy, $C_1$–$C_4$-alkylthio, $C_1$–$C_2$-fluoro-alkoxy, $C_1$–$C_2$-chlorofluoroalkoxy or $C_1$–$C_2$-fluoro-alkylthio,
$R^2$ represents hydrogen or methoxy or
$R^1$ and $R^2$ together represent $C_1$–$C_2$-alkylenedioxy or $C_1$–$C_2$-fluoro-alkylenedioxy,
$R^3$ represents chlorine and
R represents $C_{1-4}$-alkyl or the radical of an optionally substituted phenoxybenzyl alcohol of the general formula

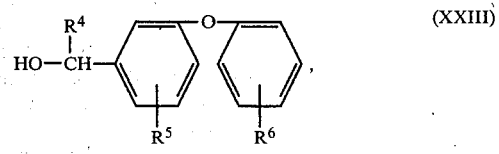  (XXIII)

wherein
$R^4$ represents hydrogen, cyano or ethynyl and
$R^5$ and $R^6$ represent hydrogen or fluorine,
provides a definition of the starting substances which can be used in process 1.

Process 1 is carried out by dissolving the compound of the formula (II) in a diluent, if appropriate, adding the catalyst and then adding the base. Examples of possible diluents are hydrocarbons, such as benzine, petroleum ether, benzene, toluene, xylene or cyclohexane; chlorinated hydrocarbons, such as methylene chloride, chlorobenzene or dichlorobenzene, or nitriles, such as acetonitrile.

Quite generally, any inert, water-immiscible diluent can be used.

The bases used are preferably aqueous bases, such as NaOH or KOH, but the water content can be very low. Thus, for example, it is also possible to use technical grade pulverulent potassium hydroxide without further addition of water. Furthermore, sodium carbonate or potassium carbonate can also be used as the base, especially when acetonitrile is used.

The process is carried out in the presence of a phase transfer catalyst.

Examples of possible phase transfer catalysts are crown ethers, tetraalkylphosphonium salts or, preferably, tetraalkylammonium salts. Very particularly preferred catalysts which may be mentioned are: tetrapropylammonium bromide, tetrabutylammonium chloride and bromide, benzyltriethylammonium chloride and methyltrioctylammonium chloride.

The amount of catalyst can vary within wide limits. In general, 0.1–15% by weight, preferably 0.3 to 10% by weight, relative to the weight of the compounds of the general formula (II) employed, have proved suitable.

The process is carried out at a temperature between −20° C. and 80° C., preferably between 0° and 50° C. At higher temperatures, an additional molecule of hydrogen chloride is split off and the desired compound of the general formula (I) is not obtained.

The reaction is preferably carried out under normal pressure.

The use of cheap aqueous bases is an important technical advance, since similar reactions can otherwise be carried out only with strong, anhydrous bases, such as, for example, sodium hydride, potassium tert.-butylate or sodium tert.-amylate (U.S. Pat. Nos. 3,652,652; and 3,077,496). Sodium hydride can be handled only with difficulty on an industrial scale; in addition, such bases give only unsatisfactory yields in similar reactions. Moreover the results are even worse in the cases in which $R^3$ represents chlorine, since hydrogen chloride can very readily be split off from the β-chloro-β-arylvinyl group with such strong bases owing to the presence of the aryl group.

An object of the invention was thus to discover a process using bases which did not cause such a splitting off under certain conditions. This is not the case, surprisingly, with the bases used according to the invention and at the reaction temperatures used in the process according to the invention. In addition it is extremely surprising that virtually no saponification of the ester group, which as is known proceeds in an alkaline medium under very mild conditions, takes place even when aqueous bases are used.

The following cyclopropanecarboxylic acid esters of the formula (I) can preferably be prepared by process 1: 2,2-dimethyl-3-[2'-chloro-2'-(4'-methoxy-phenyl)-vinyl]-cyclopropane-1-carboxylic acid methyl ester and ethyl ester, 2,2-dimethyl-3-[2'-chloro-2'-(4'-ethoxy-phenyl)-vinyl]-cyclopropane-1-carboxylic acid methyl ester and ethyl ester, 2,2-dimethyl-3-[2'-chloro-2'-(3',4'-dimethoxy-phenyl)-vinyl]-cyclopropane-1-carboxylic acid methyl ester and ethyl ester, 2,2-dimethyl-3-[2'-chloro-2'-(4'-trifluoromethoxy-phenyl)-vinyl]-cyclopropane-1-carboxylic acid methyl ester and ethyl ester, 2,2-dimethyl-3-[2'-chloro-2'-(4'-chlorodifluoromethoxy-phenyl)-vinyl]-cyclopropane-1-carboxylic acid methyl ester and ethyl ester, 2,2-dimethyl-3-[2'-chloro-2'-(3'-methoxyphenyl)-vinyl]-cyclopropane-1-carboxylic acid methyl ester and ethyl ester, 2,2-dimethyl-3-[2'-chloro-2'-(3',4'-methylenedioxy-phenyl)-vinyl]-cyclopropane-carboxylic acid methyl ester and ethyl ester, 2,2-dimethyl-3-[2'-chloro-2'-(4'-trifluoromethylthio-phenyl)vinyl]-cyclopropane-1-carboxylic acid methyl ester and ethyl ester, 2,2-dimethyl-3-[2'-chloro-2'-(3'-trifluoromethoxy-phenyl)-vinyl]-cyclopropane-1-carboxylic acid methyl ester and ethyl ester, 2,2-dimethyl-3-[2'-chloro-2'-(3', 4'-difluoromethylenedioxy-phenyl)-vinyl]-cyclopropane-1-carboxylic acid methyl ester and ethyl ester, 2,2-dimethyl-3-[2'-chloro-2'-(3',4'-trifluoroethylenedioxy-phenyl)-vinyl]-cyclopropane-1-carboxylic acid methyl ester and ethyl ester, 2,2-dimethyl-3-[2'-chloro-2'-(1,1,2,2-tetrafluoroethoxy-phenyl)-vinyl]-cyclopropane-1-carboxylic acid methyl ester and ethyl ester and 2,2-dimethyl-3-[2'-chloro-2'-(4'-trifluoromethylmercapto-phenyl)-vinyl]-cyclopropane-1-carboxylic acid methyl ester and ethyl ester.

The compounds of the general formula (II) have not hitherto been described in the literature. They are obtained by the process indicated under 4 hereinabove by reacting compounds of the general formula (III) with a halogenating agent and simultaneously or successively with an alcohol of the formula (IV), if appropriate in the presence of a diluent and if appropriate in the presence of a gaseous hydrogen halide.

If 4,4-dimethyl-3-[2'-(4'-methoxy-phenyl)-2'-chlorovinyl]-γ-butyrolactone, thionyl chloride and ethanol are used as starting substances in process 4, the course of the reaction can be represented by the following equation:

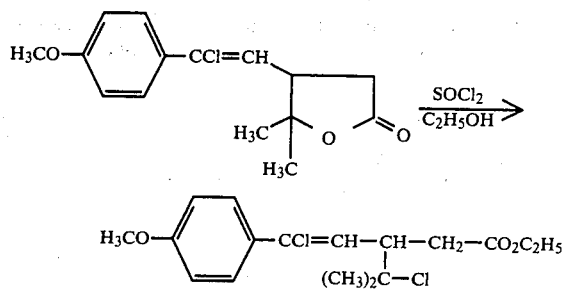

The general formula (III) provides a definition of the starting substances which can be used in process 4 hereinabove. The preferred substituents $R^1$, $R^2$ and $R^3$ are the same as those in the case of process 1. The compounds of the formula (III) have not been disclosed hitherto in the literature; their preparation is described below.

The following halogenating agents can be used in process 4: hydrogen chloride, hydrogen bromide, thionyl chloride, phosgene, phosphorus trichloride and phosphorus pentachloride. Thionyl chloride is preferred.

Preferred alcohols which can be used in process 4 are: methanol, ethanol, propanol, iso-propanol, butanol, 3-phenoxy-benzyl alcohol, 3-phenoxy-α-cyanobenzyl alcohol and 3-phenoxy-4-fluoro-α-cyano-benzylalcohol. Methanol and ethanol are very particularly preferred.

Examples of possible diluents are: benzene, toluene, benzine, petroleum ether, cyclohexane, chlorobenzene, xylene and chloroform.

The reaction temperature is in general between 30° and 150° C., preferably between 50° and 100° C.

The process can be carried out in two ways, which are in principle different.

In one method, the starting substance of the general formula (III) is dissolved in an alcohol of the formula (IV), if appropriate a diluent is also added, and the halogenating agent is then passed in or added dropwise.

However, the starting substance of the general formula (III) is preferably first heated with the halogenating agent, without addition of an alcohol, if appropriate under pressure and if appropriate in the presence of a diluent. The alcohol of the general formula (IV) is then added dropwise or pumped in, if appropriate in the presence of additional hydrogen chloride. The halogenating agent is preferably employed in excess.

The compounds of the general formula (II) are isolated by distilling off the solvent. Further purification is difficult, but also unnecessary. The crude compounds of the formula (II) can be used directly for process 1.

As stated above, the compounds of the general formula (III) are new. They are obtained by the process indicated under 6 hereinabove, by (a) reacting compounds of the formula (V) with phosphorus pentachloride, or (b) decarboxylating compounds of the formula (VI) or saponifying them to the carboxylic acid and decarboxylating the acid, or (c) reducing compounds of the formula (V) and then splitting off water.

If 4,4-dimethyl-3-(4'-trifluoromethoxy-phenacyl)-γ-butyrolactone is used as the starting substance in process 6 (a) hereinabove, the course of the reaction can be represented by the following equation:

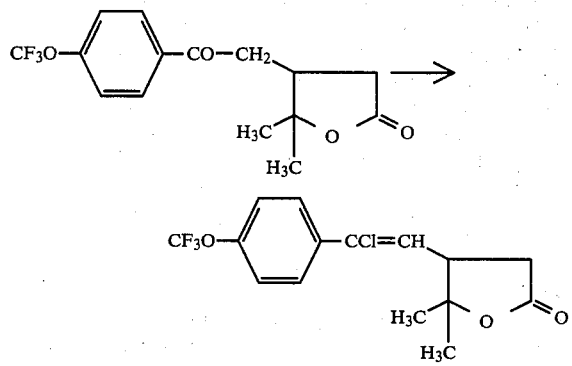

The general formula (V) provides a definition of the starting substances which can be used in process 6(a) hereinabove. The preferred substituents $R^1$ and $R^2$ are the same as those in the case of process 1.

The compounds of the formula (V) have not been disclosed hitherto in the literature. Their preparation is analogous to the preparation of 4,4-dimethyl-3-phenacyl-γ-butyrolactone, by the process indicated in J. Org. Chemistry, Volume 39, No. 17, page 2,604 (1974). However, some of these compounds can also be obtained by process 16 hereinabove.

Phosphorus pentachloride can be used as the chlorinating agent in process 6(a).

Process 6(a) is carried out by a procedure in which the starting substances of the formula (V) are reacted with 1 to 2.5 equivalents of the chlorinating agent, preferably with 1.1 to 2 equivalents.

In contrast to the generally customary procedure (Houben-Weyl, Volume V, 3, page 912 et seq.) in the reaction of ketones with phosphorus pentachloride, the reaction is preferably carried out in the presence of a diluent.

Possible diluents are, in particular, hydrocarbons, such as benzine, petroleum ether, cyclohexane, benzene or toluene, and also chlorinated hydrocarbons, such as methylene chloride, chloroform, carbon tetrachloride, dichloroethane or chlorobenzene, as well as nitriles, such as acetonitrile.

The reaction temperature is between $-20°$ C. and $+60°$ C., preferably between $0°$ C. and $35°$ C.

The reaction batch is worked up by stirring with water, separating off the organic phase and distilling off the solvent. The compound of the general formula (III) is purified by distillation or recrystallization.

If 4,4-dimethyl-3-[2-(4'-trifluoro-methoxy-phenyl)-2'-chloro-vinyl]-2-ethoxycarbonyl-γ-butyrolactone is used as the starting substance in process 6(b), the course of the reaction can be represented by the following equation:

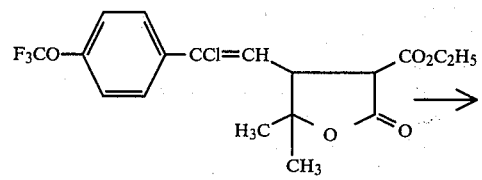

-continued

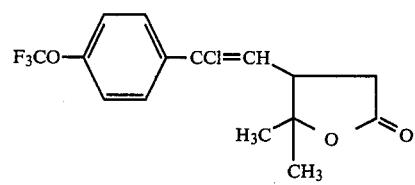

The general formula (VI) provides a definition of the starting substances which can be used in process 6(b). The preferred substituents $R^1$, $R^2$ and $R^3$ are the same as those in the case of process 1, and $R^4$ preferably represents methyl or ethyl.

The compounds of the formula (VI) have not been disclosed hitherto in the literature; their preparation is described below.

In principle, the removal of an alkoxycarbonyl group can be carried out in a neutral, acid or alkaline medium. In process 6(b), this removal is preferably carried out in a neutral or acid medium.

For this removal, the compounds of the general formula (VI) are heated to a temperature between $80°$ and $180°$ C., preferably to a temperature between $100°$ and $150°$ C., preferably in a diluent and if appropriate in the presence of an acid or of an acid catalyst.

Examples of diluents which may be mentioned are: water, dimethylsulphoxide or phosphorus-containing solvents, such as are described in DT-OS (German Published Specification) 2,638,453. Moreover, all other inert solvents with a sufficiently high boiling point are also possible. If dimethylsulphoxide or phosphorus-containing solvents are used, the reaction is preferably carried out using water and salts. If water is used exclusively as the diluent, the reaction must be carried out under pressure and the preferred temperature is above $120°$ C.

However, it is preferable to carry out the reaction in the presence of an acid or of an acid catalyst. Examples of such compounds which may be mentioned are: sulphuric acid, phosphoric acid, sulphonic acids or acid ion exchangers. In this case, either the reaction is carried out under pressure or, preferably, the alcohol $R^4$-OH formed is preferably distilled off continuously from the mixture, if appropriate together with the solvent used.

The compounds of the formula (III) are isolated in the customary manner by filtration or extraction.

As stated above, the compounds of the general formula (VI) are new. They are obtained by the process indicated under 9, by reacting compounds of the general formula (VII) with malonic esters of the formula (VIII) in the presence of a base, and if appropriate in the presence of a diluent.

If 4,4-dimethyl-3-(4'-methoxy-phenacyl)-γ-butyrolactone is used as the starting substance in process 6(c), the course of the reaction can be represented by the following equation:

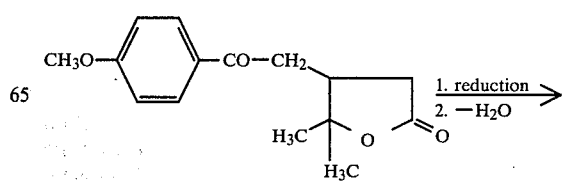

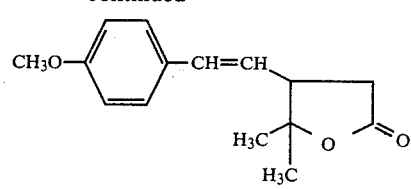

The general formula (V) provides a definition of the starting substances which can be used in process 6(c). The preferred and particularly preferred substituents $R^1$ and $R^2$ are the same as those in the case of process 1.

The first part step of process 6(c) is a reduction reaction.

In principle, possible reducing agents are any of the agents by which a ketone is reduced to the alcohol without the lactone ring being attached. Examples which may be mentioned are: a complex borohydride, such as sodium borohydride or potassium borohydride, or hydrogen in the presence of, for example, a nickel catalyst, palladium catalyst or platinum catalyst, for example Raney nickel. The use of sodium borohydride is preferred.

The second part step of process 6(c) is a dehydration. Acid catalysts are preferably employed for the dehydration. Examples which may be mentioned are: oxalic acid, sulphuric acid, phosphoric acid, potassium bisulphate, p-toluenesulphonic acid, aluminum oxide and silicates.

In addition, the alcohol formed can be acylated and acetic acid can then be split off by heating. Acetylation is effected by acetyl chloride or acetic anhydride.

If 2,2-dimethyl-3-[2'-(4'-ethoxy-phenyl)-2'-chlorovinyl]-oxirane and malonic acid dimethyl ester are used as starting substances in process 9, the course of the reaction can be represented by the following equation:

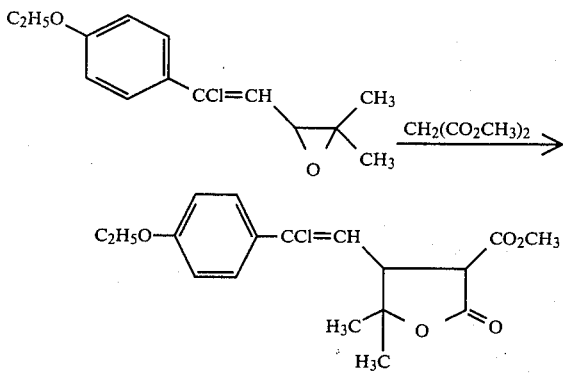

The general formulae (VII) and (VIII) provide definitions of the starting substances which can be used in process 9. The compounds of the formula (VIII) are known, and the preferred substituents $R^4$ are methyl and ethyl. The compounds of the general formula (VII) have not hitherto been disclosed in the literature. The preferred substituents $R^1$, $R^2$ and $R^3$ are the same as in the case of process 1.

The preparation of the compounds of the general formula (VII) is described below.

Process 9 is carried out by first preparing the sodium salt or potassium salt of the malonic ester of the formula (VIII), which is usually carried out with an alcoholate, such as sodium methylate or sodium ethylate. An alcohol, such as methanol or ethanol, is preferably used as the diluent.

The reaction according to process 9 is indeed known in principle, but not with the substituents used according to the invention. Process conditions under which the aryl-chloro-vinyl group, which is sensitive towards alkali, is not attached therefore had to be found.

It was found that the compounds of the formula (VI) are preferably obtained when the reaction is carried out below 50° C. The preferred reaction temperature for process 9 is thus between 0° and 50° C., especially between 20° and 40° C.

The oxirane of the general formula (VII) is added dropwise to a suspension of the malonic ester salt in a diluent at the above temperature and the reaction solution is further kept at the chosen reaction temperature for some time, usually about 1–6 hours.

The compound of the formula (VI) can be isolated by working up the mixture in the customary manner, or can be reacted further directly according to process 6(b).

As stated above, the compounds of the general formula (VII) are new. They are obtained by the process indicated under 12, by oxidizing compounds of the formula (IX).

If 1,1-dimethyl-4-(4'-trifluoro-methylthiophenyl)-4-chloro-1,3-butadiene is used as the starting substance in process 12, the course of the reaction can be represented by the following equation:

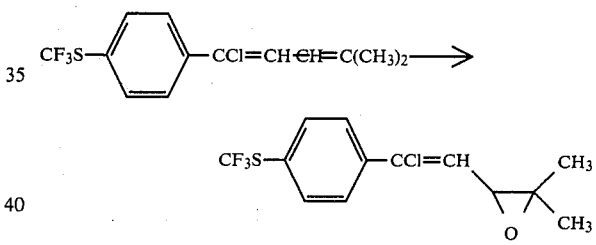

The general formula (IX) provides a definition of the starting substances which can be used in process 12. The preferred substituents are the same as those in the case of process 1.

The compounds of the formula (IX) have not hitherto been disclosed in the literature; their preparation is described below.

The conversion of a double bond into an oxirane is known in principle, but the epoxidation of dienes usually leads to only poor yields, since in principle both double bonds can be attacked.

Furthermore, the use of peracids very frequently leads to secondary reactions since oxiranes can be opened again under acid conditions.

An object of the invention was thus to discover a process using oxidizing agents which lead to the desired oxirane of the general formula (VII) in good yield and highly selectively. Surprisingly, it has been found that with aromatic peracids, in contrast to aliphatic peracids, the desired oxiranes are formed in good yield and highly selectively. This is surprising, since aromatic peracids are powerful oxidizing agents and it have been assumed that both double bonds would be attacked using these agents, as is the case with aliphatic peracids, for example perpropionic acid. Possible solvents for the oxidation are benzene, methylene chloride or chloroform. If appropriate, the oxidation can be carried out in the presence of sodium carbonate. The reaction temperature is between 0° and 50° C., and is preferably room temperature.

In principle, the desired oxiranes can also be obtained via the chlorohydrins using sodium hypochlorite and subsequently splitting off hydrogen chloride. However, this process gives somewhat poorer yields than oxidation with peracids, and furthermore, two stages are required instead of one.

The compounds of the general formula (IX) have not been described hitherto in the literature. They are obtained by the process indicated under 14, by (a) reacting compounds of the formula (X A) or (X B) or a mixture thereof with phosphorus pentachloride and then reacting the product with a base, or (b) reacting compounds of the formula (XI) and dimethylacrolein of the formula (XII), or (C) reacting compounds of the formula (XVII) with the compound of the formula (XVIII), or (d) reacting compounds of the formula (XVII) wth isopropylmagnesium chloride.

If a mixture of 2-methyl-5-oxo-5-(4'-methoxy)phenyl-2-pentene and 2-methyl-5-oxo-5-(4'-methoxy)phenyl-3-pentene is used as the starting substance in process 14(a), the course of the reaction can be represented by the following equation:

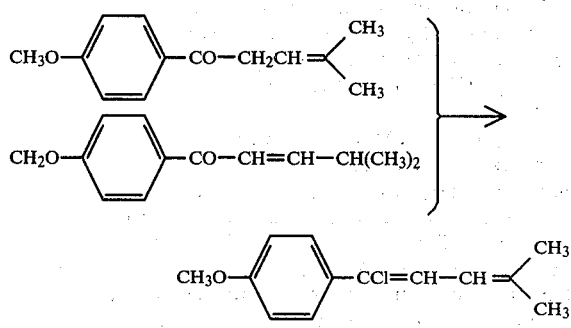

The formula (X A) and (X B) provide general definitions of the starting substances which can be used in process 14(a). The preferred substituents $R^1$ and $R^2$ are the same as those in the case of process 1.

The compounds of the formula (X) have not been described before in the literature. Their preparation is carried out analogously to the process described in J. Org. Chemistry, Volume 25, page 272. Condensation of the acetophenones of the formula (XVI) with isobutyraldehyde gives dimeric products, which are split into a mixture of monomers of the formula (X A) and (X B) by distillation in the presence of sodium acetate:

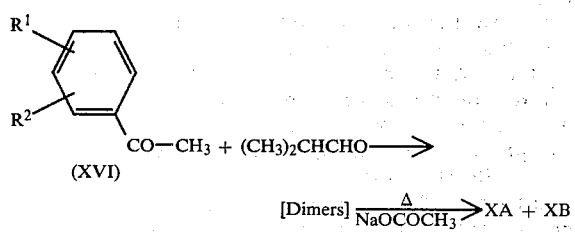

Examples of acetophenones of the formula (XVI) which may be mentioned are: 4-ethoxyacetophenone, 4-methylmercaptoacetophenone, 4-methoxyacetophenone and 3,4-dioxymethyleneacetophenone.

Process 14(a) is carried out by a procedure in which the starting substance of the general formula (X A) or (X B), or a mixture of the two, is initially introduced in a diluent and $PCl_5$ is metered in.

In contrast to the generally customary procedure in the reaction of ketones with phosphorus pentachloride (Houben-Weyl, Volume V, 3, page 912 et seq.), process 14(a) is preferably carried out in the presence of a diluent. Examples of possible diluents are hydrocarbons, such as benzine, petroleum ether, pentane, hexane, cyclohexane, benzene, toluene or xylene; chlorinated hydrocarbons, such as methylene chloride, carbon tetrachloride, dichloroethane or chlorobenzene; and nitriles, such as acetonitrile. Toluene, cyclohexane and carbon tetrachloride are preferred.

The reaction of an unsaturated ketone with $PCl_5$ virtually always presents problems and gives rise to a number of side reactions.

Thus, for example, $PCl_5$ can cause chlorination in the alkyl position or in the α-position relative to the carbonyl group. The hydrogen chloride formed in this reaction and by elimination can add on to a double bond again. In addition, $PCl_5$ is also capable of chlorinating double bonds, so that products with a higher degree of chlorination are formed.

It has been found that these side reactions can be avoided virtually completely if the reaction is carried out in the presence of a diluent and at a relatively low temperature, and a base is then added at the same temperature or at a lower temperature, so that the presence of hydrogen chloride at a relatively high temperature is avoided.

Process 14(a) is carried out at a temperature beween −40° C. and +30° C., and a temperature between −10° C. and +20° C. is preferred.

Possible bases are alcoholates, such as sodium methylate or sodium ethylate. An aqueous base, such as sodium hydroxide, sodium carbonate or potassium carbonate, in the presence of a phase-transfer catalyst, is particularly preferred.

The phase-transfer catalysts employed are preferably the same as those in the case of process 1.

The base is employed in about four times the equimolar amount, since it reacts with the phosphorus oxychloride and also serves to eliminate the hydrogen chloride.

The dienes of the general formula (IX) can be purified by distillation. If the diene cannot be distilled without decomposition, it is purified by so-called "incipient distillation", that is to say by prolonged heating to moderately elevated temperatures under reduced pressure.

If 4-trifluoromethylmercapto-α-chlorobenzyl-0,0-diethyl-phosphonic acid ester and dimethylacrolein are used as starting substances in process 14(b), the course of the reaction can be represented by the following equation:

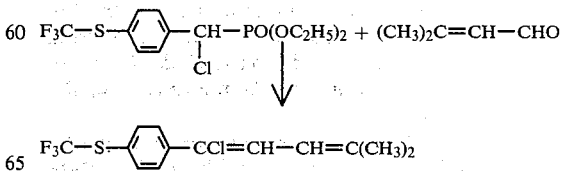

The formulae (XI) and (XII) provide definitions of the starting substances which can be used in process 14(b). Dimethylacrolein (XII) is known from the literature.

α-Chloro-benzyl-phosphonic acid esters of the formula (XI) are known. They can all be prepared by reacting α-hydroxy-benzyl-phosphonic acid esters of the general formula

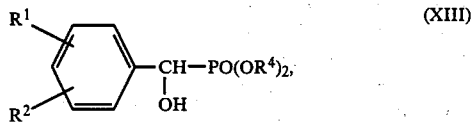

in which

R¹, R² and R⁴ have the meanings indicated under 14, with a chlorinating agent, for example thionyl chloride or phosphorus oxychloride, at a temperature between 0° and 100° C., preferably at from 20° to 80° C. (see Chimia 28 (1974), 656–657; and J. Am. Chem. Soc. 87 (1965), 2,777–2,778).

Formula (XIII) provides a definition of the α-hydroxy-benzyl-phosphonic acid esters to be used for the preparation of the starting compounds of the formula (XII).

α-Hydroxy-benyl-phonphobic acid esters of the fomula (XIII) are known. They can all be obtained by known processes, in general by reacting aldehydes of the general formula

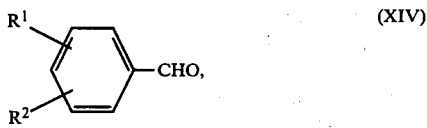

wherein

R¹ and R² have the meanings indicated above, with phosphorous acid esters of the general formula

wherein

R⁴ has the meaning indicated above,
if appropriate in the presence of a catalyst, for example triethylamine, at a temperature between 0° and 150° C., preferably at from 20° to 100° C. (see Houben-Weyl, Methoden der organischen Chemie (Methods of Organic Chemistry), 4th edition (1963), Volume 12/1, pages 475–483, Georg Thieme Verlag, Stuttgart).

Examples of aldehydes of the formula (XIV) which may be mentioned are: 4-methoxybenzaldehyde, 4-trifluoromethoxybenzaldehyde, 4-trifluoromethylmercaptobenzaldehyde, 5-formyl-2,2-difluoro-1,3-benzodioxole and 5-formyl-1,3-benzodioxole (piperonal).

Examples of the phosphorous acid esters of the formula (XV) which may be mentioned are: phosphorous acid dimethyl ester and phosphorous acid diethyl ester.

Process 14(b) is a variant of the Wittig reaction and is known in principle.

Thus, for example, chloro-styryl compounds are obtained when aldehydes are reacted with α-chloro-benzyl-phosphoric acid esters in the presence of a base (Chimia 28, pages 656–657; 1974 and J. Am. Chem. Soc. 87, pages 2,777–2,778; 1965).

According to the state of the art, the base used for this reaction is sodium hydride, an expensive reagent which is difficult to handle. The application of this synthesis method has hitherto been restricted to only a few examples.

In contrast, the process according to the invention is considerably less expensive to carry out. It is simpler and can also be carried out on an industrial scale without problems.

Further advantages of the process according to the invention which may be mentioned are, for example, the possibility of carrying out the process at room temperature and in water-containing reaction media, the possibility of using relatively cheap bases instead of sodium hydride, the comparatively simple working up and the good yields.

In general, process 14(b) for the preparation of compounds of the formula (IX) is carried out using a diluent. Possible diluents are virtually any of the inert organic solvents. These include, as preferences, aliphatic and aromatic, optionally chlorinated hydrocarbons, such as benzine, benzene, toluene, xylene, methylene chloride, chloroform, carbon tetrachloride, chlorobenzene and α-dichlorobenzene; ethers, such as diethyl ether, dibutyl ether, tetrahydrofuran and diocane; alcohols, such as methanol, ethanol, n- and iso-propanol and n-, iso-, sec.- and tert.-butanol; and dimethylsulphoxide.

When the reaction is carried out in a two-phase medium, a virtually water-immiscible solvent, for example benzine, benzene or toluene, is used, in general in addition to 50% strength aqueous sodium hydroxide solution.

The bases customarily for carbonyl olefination reactions can be used as the bases. Bases which may be mentioned are alkali metal hydroxides, for example sodium hydroxide and potassium hydroxide; alkali metal alcoholates, for example sodium methylate, ethylate, n- and iso-propylate and n-, iso-, sec.- and tert.-butylate and potassium methylate, ethylate, n- and iso-propylate and n-, iso-, sec.- and tert.-butylate; alkali metal hydrides, for example sodium hydride; and alkyl-lithium compounds, for example, butyl-lithium.

Sodium hydroxide, potassium hydroxide, sodium methylate or sodium ethylate is preferably used as the base.

In general, the reaction temperatures are between −70° C. and +150° C., preferably between −10° and +50° C. The reaction is in general carried out under normal pressure.

The reactants are usually employed in equimolar amounts for carrying out the process according to the invention. Only the bases are usually employed in a larger excess: when the reaction is carried out in a single-phase system, up to 30 mol %, preferably up to 15 mol % excess; and when 50% strength sodium hydroxide solution is used as the second phase, in general 5 to 15 times the stoichiometrically required amount.

If appropriate, alcoholates are prepared in situ from the alcohols and alkali metals.

In general, the base and, if appropriate, the catalyst are initially introduced in one or more of the diluents mentioned. The reactants—α-chloro-benzyl-phosphonic acid ester and aldehyde—if appropriate dissolved in one of the solvents indicated, are added to this initial mixture in the sequence indicated. The mixture is kept in the temperature range indicated for several hours, while stirring, to bring the reaction to completion.

For working up, water is added to the reaction mixture and the mixture is acidified, if appropriate, with hydrochloric acid and extracted with methylene chloride. The organic phase is dried and the solvent is distilled off in vacuo. The product which remains in the residue is purified, if appropriate, by vacuum distillation, or if it cannot be distilled without decomposition, by so-called "incipient distillation", that is to say by prolonged heating to moderately elevated temperatures under reduced pressure. The boiling point or the refractive index is used for characterization.

If β-(3,4-methylenedioxy-phenyl)-β-chloro-acrolein and triphenylisopropylphosphorane are used as starting substances in process 14(c), the course of the reaction can be represented by the following equation:

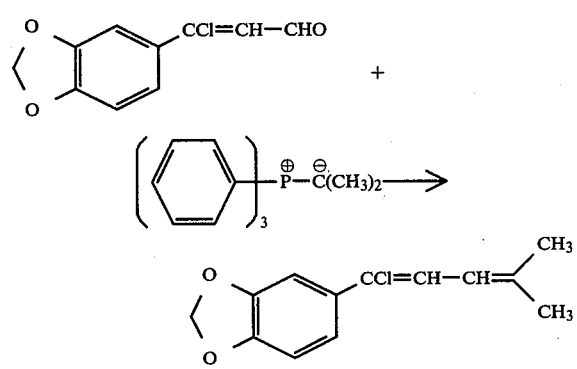

The preparation of the phosphorane of the formula (XVIII) is known. Aldehydes of the general formula (XVII) are known. The preparation of the aldehydes (XVII) by a new process is described below.

The general formula (XVII) provides a definition of the starting substances which can be used in process 14(c) and process 14(d). The preferred substituents are the same as those in the case of process 1.

Examples of the aldehydes of the formula (XVII) which may be mentioned are: β-(4-methoxyphenyL)-β-chloroacrolein and β-(3,4-methylenedioxy-phenyl)-β-chloroacrolein.

Process 14(c) is a Wittig reaction and is carried out by methods which are known in principle.

If β-(4-methoxy-phenyl)-β-chloroacrolein and isopropyl-magnesium chloride are used as starting substances in process 14(d), the course of the reaction can be represented by the following equation:

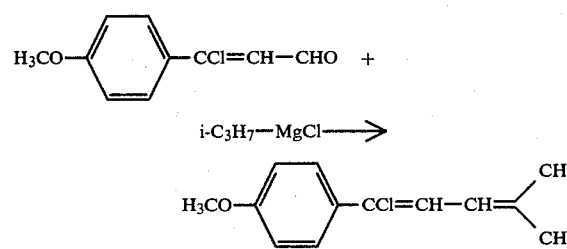

The preparation of isopropyl-magnesium chloride (XIX) is known: see Chem. Ber. 69 (1936), page 1,766.

Process 14(d) is a Grignard reaction with a subsequent dehydration. The Grignard reaction is carried out in a manner which is known in principle. It is surprising that water can be split off relatively easily from the secondary alcohol formed as an intermediate.

The dehydration is effected with an acid, preferably with sulphuric acid, at a temperature between 0° and 50° C., preferably at 20° to 45° C. The dienes are isolated by pouring the mixture into water and extracting in the customary manner.

If 4-methoxy-acetophenone is used as the starting substance in process 15 (above), the course of the reaction can be represented by the following equation:

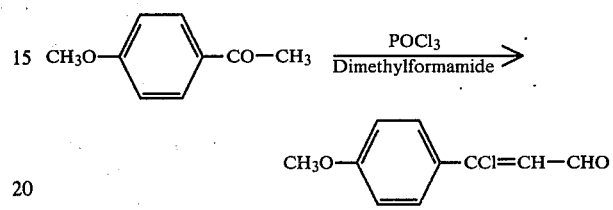

The general formula (XVI) provides a definition of the starting substances which can be used in process 15. The preferred substituents are the same as those in the case of process 1.

Examples of acetophenones of the formula (XVI) which may be mentioned are: 4-ethoxy-acetophenone, 4-methoxyacetophenone and 3,4-dioxymethyleneacetophenone.

It has been found that the β-chloroacroleins of the general formula (XVII) are obtained in a particularly simple manner and in a better yield and purity by process 15 when the addition of a diluent and the wasteful working up by distillation which are recommended in the literature (Proc. Chem. Soc. (London), 1958, 227; Angew, Chem. 71 (1959), 573; Chem. Ber. 93 (1960), 2,746; and Chem. Ber. 98 (1965), 3,554) are dispensed with and the substance is isolated as crystals, after gentle hydrolysis at a low temperature.

In the process according to the invention, a procedure is followed in which the acetophenone of the general formula (XVI) is dissolved in dimethylformamide, phosphorus oxychloride is added dropwise at 15°-100° C., preferably at 25°-60° C., and stirring is continued at the same temperature for a further 1-5 hours.

The mixture is then poured into ice-water and adjusted to a pH value of about 5 with sodium hydroxide solution. The temperature should not rise above 25° C. during this procedure. After subsequently stirring for some time, the product is filtered off, washed with water and dried in vacuo.

If anisole and 4,4-dimethyl-3-chloro-carbonylmethyl-γ-butyrolactone are used as starting substances in process 16, the course of the reaction can be represented by the following equation:

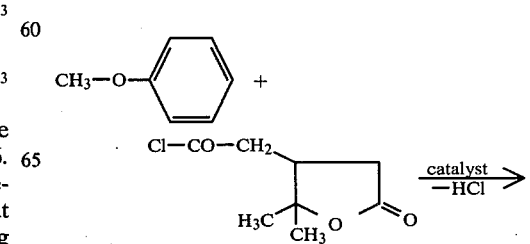

-continued

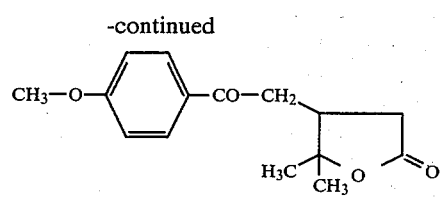

The formulae (XX) and (XXI) provide definitions of the starting substances which can be used in process 16. Compound (XX) is new; its preparation is described below.

The compounds of the formula (XXI) are known, and examples which may be mentioned are: anisole, ethoxybenzene, benzodioxole and pyrocatechol dimethyl ether.

Possible catalysts are in principle any of the customary Friedel-Crafts catalysts, such as aluminum chloride, tin tetrachloride, titanium tetrachloride, hydrogen fluoride, boron trifluoride, iron (III) chloride, zinc chloride, polyphosphoric acids, perfluoroalkanesulphonic acid (optionally in polymeric form) and, if appropriate, mixtures thereof. The process is preferably carried out in the presence of a diluent. Possible diluents are: methylene chloride, chloroform, dichloroethane, tetrachloroethane, nitrobenzene and nitromethane. Methylene chloride is preferred.

The reaction according to the invention is extremely surprising, since it had to be expected that the lactone ring would also react, in the following manner:

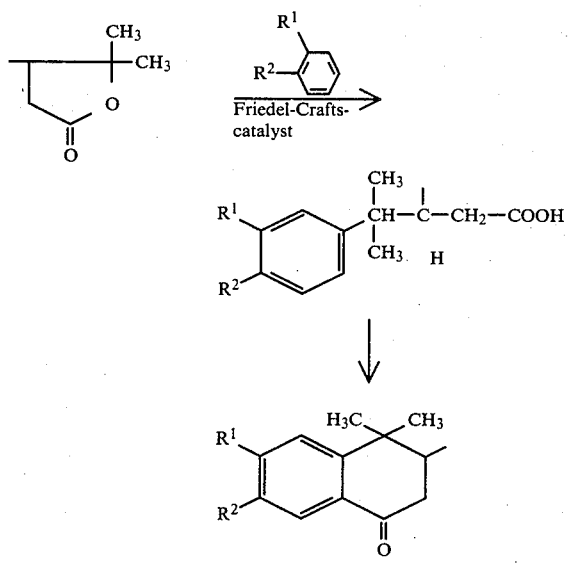

In some cases, cyclization to the tetralone could also be expected to take place. Ring openings of 5-membered lactone rings with aromatics by a Friedel-Crafts reaction in the manner formulated above are known and take place under very mild conditions (Houben-Weyl; Volume VI, 2, page 812 et seq.). That such a reaction of the lactone with the aromatics of the formula (XXI) does not take place is also surprising, especially since the Friedel-Crafts catalyst must be employed in at least an equimolar amount, and even better in excess.

In order to allow process 16 to proceed in the desired manner, the procedure is as follows:

The acid chloride (XX) is initially introduced in a diluent, and the Friedel-Crafts catalyst is added at a temperature between −10° and +5° C. The aromatic compound, if appropriate also dissolved in a diluent, is then added dropwise. If very active Friedel-Crafts catalysts are used, this addition is carried out at from −10° to +5° C. (for example with aluminum chloride or tin tetrachloride), and in the case of less active Friedel-Crafts catalysts (for example zinc chloride, iron chloride, titanium tetrachloride or perfluoroalkanesulphonic acids), the aromatic compound is added dropwise at room temperature. The mixture is then subsequently stirred at room temperature; in the case of less active catalysts, the reaction must be carried out at elevated temperature if necessary.

The mixture is worked up in the customary manner: the lactones can be purified by recrystallization.

Process 17 can be represented by the following equation:

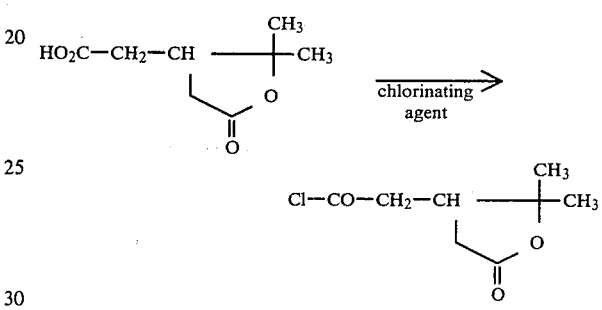

The acid of the formula (XXII) used as the starting substance is known. It is called "terpenylic acid" and can be obtained by oxidizing turpentine oil. The acid chloride of the formula (XX) is new. It is surprising that the conversion of the acid into the acid chloride takes place smoothly, since ring opening of the lactone usually also takes place under these conditions.

Process 17 is carried out under the conditions which are customary for the preparation of an acid chloride from an acid. Preferred chlorinating agents are thionyl chloride and phosgene. Care must be taken however, that the reaction times applied are as short as possible, in order to avoid a side reaction in the abovementioned sense. The mixture is worked up in the customary manner. The acid chloride can be purified by distillation or can be employed in process 16 in the crude form.

The styrylcyclopropanecarboxylic acid esters of the formula (I) which contain a radical of an alcohol customary in pyrethroids are well tolerated by plants, have a favorable level of toxicity to warm-blooded animals, and can be used for combating arthropod pests, especially insects and acarids which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni,* Carpocapsa pomonella, Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, or example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.0001 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The present invention also provides an arthropodicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects or acarids) which comprises applying to the arthropods, or to a habitat thereof, a compound of the present invention alone or in the form of a composition containing as active ingredient a compound of the present invention in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that the usual methods of providing a harvested crop may be improved by the present invention.

The invention is further described in the following illustrative examples

EXAMPLE 1 (Process 1)

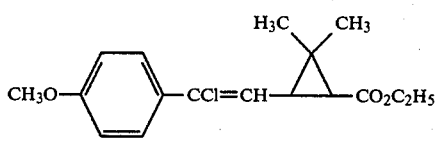 (1)

34.5 g of 5-(4'-methoxy-phenyl)-5-chloro-3-(1'-chloro-1'-methyl)-ethyl-pent-4-enoic acid ethyl ester were dissolved in 200 ml of toluene, and 5 g of tetrabutylammonium bromide were added. The mixture was then heated to about 30° C. and 56 g of 50% strength potassium hydroxide solution were added dropwise in the course of 30 minutes. During this addition, the temperature was kept at about 30°–35° C. The mixture was then subsequently stirred at 35° C. for a further 2 hours, 200 g of ice-water were added and the organic phase was separated off. The aqueous phase was extracted by shaking twice more with 50 ml of toluene each time and the combined organic phases were washed neutral with water, to which about 1 N HCl was added, dried with $Na_2SO_4$ and evaporated on a rotary evaporator. Distillation under a high vacuum gave 25 g of crude 2,2-dimethyl-3-[2'-chloro-2'-(4'-methoxy-phenyl)-vinyl]-cyclopropane-1-carboxylic acid ethyl ester (isomer mixture; one of the four isomers was formed to a very predominant extent), which could be purified still further by a second distillation. Boiling point: 162°–168° C./0.08 mbar.

The following compounds were obtained analogously (process 1): 2,2-dimethyl-3-[2'-chloro-2'-(4'-trifluoromethoxy-phenyl)-vinyl]-cyclopropane-1-carboxylic acid ethyl ester and 2,2-dimethyl-3-[2'-chloro-2'-(3',4'-methylenedioxy-phenyl)-vinyl]-cyclopropane-1-carboxylic acid ethyl ester.

EXAMPLE 2 (Process 4)

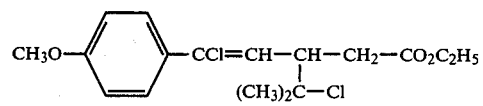

141.0 g of 4,4-dimethyl-3-[2'-chloro-2'-(4'-methyoxy-phenyl)-vinyl]-γ-butyrolactone were dissolved in 500 ml of toluene. 125 ml of thionyl chloride were then added and the mixture was heated to 80° C. for 6 hours. A further 125 ml of thionyl chloride were then added and the mixture was heated again to 80° C. The excess thionyl chloride and a little toluene were then distilled off (about 250 ml) under normal pressure, with exclusion of water. After cooling, 400 ml of ethanol, which was saturated with hydrogen chloride, were added dropwise at 20° C. in the course of 3 hours, while cooling. The mixture was subsequently stirred for a further 3 hours and left to stand overnight. The solvents were distilled off under reduced pressure (waterpump vacuum). The crude 5-(4'-methoxy-phenyl)-5-chloro-3-(1'-chloro-1'-methyl)-ethyl-pent-4-enoic acid ethyl ester which remained was further reacted directly according to process 1.

The following compounds were obtained analogously (process 4): 5-(4'-trifluoromethoxy-phenyl)-5-chloro-3-(1'-chloro-1'-methyl)-ethyl-pent-4-enoic acid ethyl ester and 5-(3,4'-methylenedioxy-phenyl)-5-chloro-3-(1'-chloro-1'-methyl)-ethyl-pent-4-enoic acid ethyl ester.

EXAMPLE 3 (Process 4)

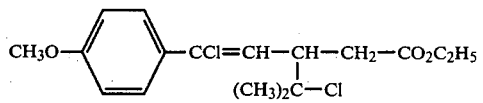

134 g of 4,4-dimethyl-3-[2'-chloro-2'-(4'-methoxyphenyl)-vinyl]-γ-butyrolactone were mixed with 120 g of thionyl chloride in a 0.7 liter autoclave. 50 g of ethanol were then pumped in. The autoclave was then heated to 80° C. for a further 1 hour, and was allowed to cool and was let down. Excess thionyl chloride and sulphuric acid ethyl ester were removed by distillation under a waterpump vacuum. The residue consisted essentially of 5-(4'-methoxy-phenyl)-5-chloro-3-(1'-chloro-1'-methyl)-ethyl-pent-4-enoic acid ethyl ester and was further reacted directly according to process 1.

EXAMPLE 4 (Process 6(a))

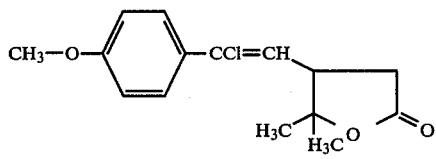

52.4 g of 4,4-dimethyl-3-(4'-methoxy-phenacyl)-γ-butyrolactone were dissolved in 300 ml of toluene, 87 g of phosphorus pentachloride were metered in and the mixture was subsequently stirred at room temperature until everything had dissolved (about 8 hours). 500 ml of water were then added dropwise at 20°-50° C. and stirring was continued for 4 hours. The toluene phase was then separated off, dried with sodium sulphate and concentrated under a waterpump vacuum. 4,4-Dimethyl-3-[2'-chloro-2'-(4'-methoxy-phenyl)-vinyl]-γ-butyrolactone (E and Z isomer) remained.

EXAMPLE 5 (Process 6(b))

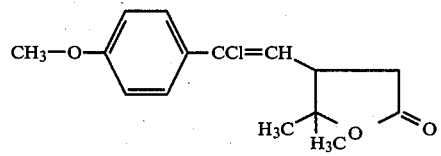

40 g of crude 4,4-dimethyl-3-[2'-chloro-2'-(4'-methoxy-phenyl)-vinyl]-2-ethoxycarbonyl-γ-butyrolactone were suspended in 400 ml of 25% strength sulphuric acid, and water and ethanol were distilled off under normal pressure until the internal temperature had reached 115°-120° C. The mixture was then heated at this temperature (without further distillation) for a further 10 hours and was allowed to cool and was extracted with methylene chloride. After drying the methylene chloride extract with sodium sulphate and stripping off the solvent, a dark residue, which partly crystallized after standing for a short time, remained. On the basis of the NMR spectrum, the residue was 4,4-dimethyl-3-[2'-chloro-2'-(4'-methoxyphenyl)-vinyl]-γ-butyrolactone (E and Z isomer).

The following compounds were obtained analogously (process 6(b)): 4,4-dimethyl-3-[2'-chloro-2'-(4'-trifluoromethoxy-phenyl)-vinyl]-γ-butyrolactone and 4,4-dimethyl-3-[2'-chloro-2'-(3',4'-methylenedioxyphenyl)-vinyl]-γ-butyrolactone.

EXAMPLE 6 (Process 9)

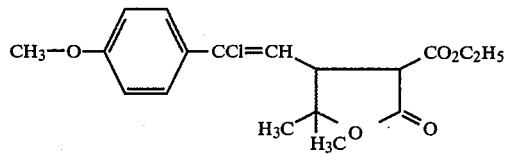

3.5 g of sodium were dissolved in 350 ml of ethanol, and 24 g of malonic acid diethyl ester were added dropwise at room temperature. 35.8 g of 2,2-dimethyl-3-[2'-chloro-2'-(4'-methoxyphenyl)-vinyl]-oxirane were then slowly added dropwise at 30°-35° C. When the dropwise addition had ended, the mixture was kept at 35° C. for a further 4 hours and was then allowed to cool. (At this point, if desired, process 6(b) could follow directly).

Some of the ethanol was distilled off in vacuo, icewater was added and the mixture was rendered acid. It was then extracted with methylene chloride, the organic phase was dried with sodium sulphate and the solvent was distilled off. The residue weighed 39 g and consisted, as proved by the IR spectrum, NMR spectrum and mass spectrum, mainly of 4,4-dimethyl-3-[2'-chloro-2'-(4'-methoxyphenyl)-vinyl]-2-ethoxycarbonyl-γ-butyrolactone.

The following compounds were obtained analogously (process 9): 4,4-dimethyl-3-[2'-chloro-2'-(4'-trifluoromethoxyphenyl)-vinyl]-2-ethoxycarbonyl-γ-butyrolactone and 4,4-dimethyl-3-[2'-chloro-2'-(3',4'-methylenedioxyphenyl)-vinyl]-2-ethoxycarbonyl-γ-butyrolactone.

EXAMPLE 7 (Process 12)

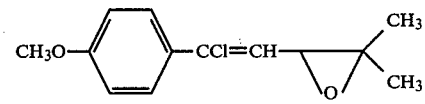

89 g (0.4 mol) of 1-(4'-methoxyphenyl)-1-chloro-4,4-dimethyl-1,3-butadiene were dissolved in 640 ml of methylene chloride, and 160 g of powdered anhydrous sodium carbonate were added. 69 g (0.4 mol) of m-chloro-perbenzoic acid were then metered in at room temperature and the mixture was subsequently stirred at room temperature for 2 hours. The solid was then filtered off and rinsed with $CH_2Cl_2$ and the methylene chloride solution was extracted by shaking twice with a large quantity of sodium bicarbonate solution. After washing the methylene chloride phase with water until neutral, it was dried with $Na_2SO_4$ and concentrated on a rotary evaporator. According to the gas chromatogram, the pale yellow liquid residue ($n_D^{20}=1.481$) contained three components with the mass m/e=238 (gas chromatogram/mass spectrum). The content of the desired stereoisomeric epoxides was 91%. The product (80 g) was employed directly in the next stage. The following compounds were obtained analogously (process 12): 2,2-dimethyl-3-[2'-chloro-2'-(4'-trifluoromethoxyphenyl)-vinyl]oxirane and 2,2-dimethyl-3-[2'-chloro-2'-(3',4'-methylenedioxy-phenyl)-vinyl]oxirane.

EXAMPLE 8 (Process 14(a))

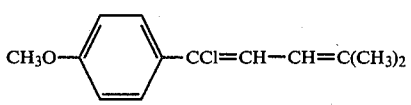

17 g of potassium hydroxide were dissolved in 125 ml of water and 125 ml of methanol, and 150 g of 4-methoxyacetophenone were added. 80 g of isobutyraldehyde were added dropwise (in the course of 1.5 hours) at 50° C. After 3.5 hours, the mixture was cooled to room temperature and neutralized with acetic acid (about 20 ml). The dimeric condensation product was filtered off, washed with methanol and dried in air. Yield: 175 g. The solid was mixed with 5 g of sodium acetate and the mixture was distilled under a waterpump vacuum. 165 g of a yellow oil which solidified at room temperature and was a mixture of 2-methyl-5-oxo-5-(4'-methoxyphenyl)-2-pentene and 2-methyl-5-oxo-5-(4'-methoxyphenyl)-3-pentene were obtained. Boiling point of the isomer mixture=158°-165° C./17 mbars.

102 g (0.5 mol) of the isomer mixture obtained above were dissolved in 500 ml of toluene, and 104 g of phosphorus pentachloride were slowly metered in at 0° C. The mixture was stirred at 0°-10° C. until all the PCl$_5$ had dissolved, 5 g of tetrabutylammonium bromide were added and 224 g (2 mol) of 50% strength potassium hydroxide solution were added dropwise at 0°-10° C., while cooling well. The toluene phase was then separated off immediately, washed until neutral and concentrated on a rotary evaporator. The crude diene was then distilled over (boiling point=125°-165° C./0.8 mm Hg) and then purified by a second distillation. 75 g of 1-(4'-methoxy-phenyl)-1-chloro-4,4-dimethyl-1,3-butadiene of boiling point 112°-119° C./0.2 mm Hg were obtained.

EXAMPLE 9 (Process 14(b))

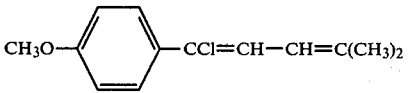

4.6 g (0.2 mol) of sodium were dissolved incrementally in 100 ml of dry ethanol. When all the sodium had dissolved, 100 ml of anhydrous tetrahydrofuran were added and 58.4 g (0.2 mol) of 4-methoxy-α-chloro-benzyl-phosphonic acid diethyl ester, dissolved in 50 ml of anhydrous tetrahydrofuran, were added dropwise at 0° C., while stirring. After stirring had been continued at 0°-10° C. for a further 1 hour, 16.8 g (0.2 mol) of β,β-dimethylacrolein, dissolved in 30 ml of anhydrous tetrahydrofuran, were added dropwise, while stirring. Stirring was then continued at room temperature for a further 12 hours. 600 ml of water were then added to the reaction mixture and the mixture was extracted twice with 300 ml of methylene chloride each time. The organic phase was separated off and dried over magnesium sulphate, the solvent was distilled off under a waterpump vacuum and the residue was distilled in vacuo. 25 g of 1-(4'-methoxyphenyl)-1-chloro-4,4-dimethyl-1,3-butadiene (isomer mixture) were obtained as a yellow oil which had a boiling point of 130°-145° C./2 mm Hg and partially crystallized after some time.

EXAMPLE 10

The following compound was obtained analogously to Example 9: 1-(3',4'-methylenedioxy-phenyl)-1-chloro-4,4-dimethyl-1,3-butadiene, of the formula

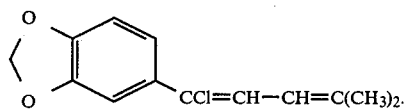

The α-hydroxy-4-methoxy-benzyl-phosphonic acid esters of the formula (XIII) required as precursors could be prepared, for example, as follows:

EXAMPLE 11

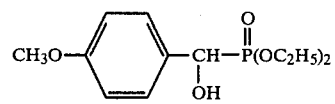

20.4 g (0.150 mol) of 4-methoxybenzaldehyde were metered into a mixture of 20.7 g (0.15 mol) of diethyl phosphite and 1.09 g (0.0109 mol) of triethylamine at 50°-70° C. in the course of one hour, while cooling with water. The reaction batch was subsequently stirred at 70° C. for 1 hour. After cooling, the batch was taken up in 40 g of toluene and the toluene mixture was rinsed several times with dilute hydrochloric acid and cold water. The organic layer was separated off and freed from solvent in vacuo. The yield was 37 g of 4-methoxy-α-hydroxy-benzyl-phosphonic acid diethyl ester.

EXAMPLE 12

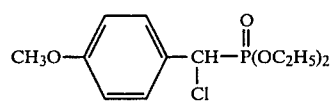

9.2 g (0.0768 mol) of thionyl chloride were added to a mixture of 20.2 g (0.0725 mol) of 4-methoxy-α-hydroxy-benzyl-phosphonic acid diethyl ester, 65 g of methylene chloride and 5.8 g (0.0725 mol) of pyridine at 20°-40° C. in the course of about 1 hour, while cooling slightly with water. The reaction mixture was then heated under reflux for 3 hours and subsequently stirred for 12 hours, without further action of heat. The mixture was poured into about 100 g of ice-water and the organic phase was separated off and dried. After distilling off the solvent, the residue was concentrated under 6 mm Hg and at 45° C. 21 g (97.7% of theory) of 4-methoxy-α-chlorobenzyl-phosphonic acid diethyl ester were obtained as a yellow viscous oil with a purity of 98.6% (gas chromatogram) and with a refractive index of n$_D^{24}$: 1.5118.

EXAMPLE 13 (Process 14(c))

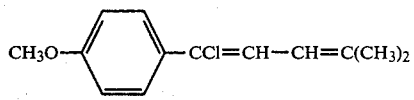

0.055 mol of n-butyl-lithium in 30 ml of hexane was added dropwise to a suspension of 22.7 g (0.0525 mol) of triphenylisopropyl-phosphonium iodide in 100 ml of tetrahydrofuran at 0° C. The mixture was subsequently stirred at 0° C. for 1 hour. A solution of 10 g (0.05 mol) of β-(4-methoxy-phenyl)-β-chloro-acrolein in 100 ml of tetrahydrofuran was then added in one operation and stirring was then continued at 20° C. for 10 hours. Thereafter, the reaction mixture was concentrated, 100 ml of water were added and the mixture was extracted twice with 50 ml of ether each time. The combined ether extracts were dried over Na₂SO₄ and concentrated. A residue which crystallized when about 50 ml of petroleum ether were added remained. The crystals were filtered off and recrystallized once more from petroleum ether. 8 g of 1-(4'-methoxyphenyl)-1-chloro-4,4-dimethyl-1,3-butadiene were obtained in the form of light yellow crystals.

EXAMPLE 14 (Process 14(d))

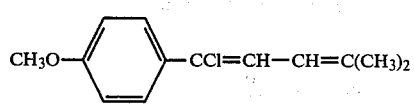

39.3 g (0.2 mol) of β-chloro-β-(4-methoxyphenyl)-acrolein in 200 ml of tetrahydrofuran were added dropwise to a solution of 0.4 mol of isopropyl-magnesium chloride in 40 ml of isopropyl chloride (prepared in accordance with the method of J. Houben et al., Chem. Ber. 69 (1936), 1766) at 20° C. The reaction mixture was subsequently stirred for 12 hours. It was then poured into a mixture of 500 g of ice and 100 ml of H₂SO₄, while stirring. The mixture was extracted twice with 100 ml of ether each time. The combined ether extracts were dried over sodium sulphate and concentrated at 50° C. in a rotary evaporator.

The residue was taken up in 50 ml of glacial acetic acid. 2 ml of concentrated H₂SO₄ were added dropwise to this solution such that the temperature did not rise above 45° C. The reaction mixture was subsequently stirred at 20° C. for 4 hours. It was then poured into water. The mixture was extracted twice with 100 ml of ether each time. The combined ether extracts were dried over Na₂SO₄, concentrated and distilled. 22 g of 1-(4'-methoxyphenyl)-1-chloro-4,4-dimethyl-1,3-butadiene were obtained in the form of a yellow oil which, on cooling, partially crystallized. Boiling point=140°-145° C./4 mm Hg.

EXAMPLE 15 (Process 15)

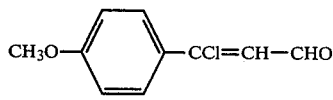

750 g (5 mol) of 4-methoxyacetophenone were dissolved in 2.5 liters of dimethylformamide, 1,570 g of phosphorus oxychloride were added dropwise at 40°-45° C. in the course of 2 hours, while cooling slightly, and the mixture was stirred for 1 hour, discharged onto 25 liters of ice-water and adjusted to a pH value of 5 by adding about 2.1 liters of concentrated sodium hydroxide solution dropwise. The temperature was kept below 25° C. during the neutralization by adding ice. Stirring was then continued at pH 5 and at a temperature below 25° C. for a further 1 hour. The light crystalline precipitate was filtered off, washed thoroughly with water and dried at 50° C. in vacuo. Yield: 730 g.

EXAMPLE 16 (Process 16)

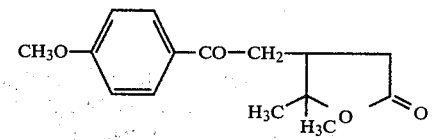

80 g of aluminum chloride were initially introduced into 300 ml of methylene chloride, and 59 g of 4,4-dimethyl-3-chlorocarbonylmethyl-γ-butyrolactone in 150 ml of methylene chloride, dissolved at 0°–5° C., were added dropwise. 32.4 g of anisole, dissolved in 50 ml of methylene chloride, were then added dropwise, also at 0°–5° C. The mixture was then allowed to come to room temperature and was subsequently stirred at room temperature for a further 7 hours. After pouring the batch into ice-water, the organic phase was separated off and washed until neutral. After drying and distilling off the solvent as well as the excess anisole, 78 g of crude 4,4-dimethyl-3-(4'-methoxy)phenacyl-γ-butyrolactone were obtained. Melting point: 83° C.

EXAMPLE 17 (Process 16)

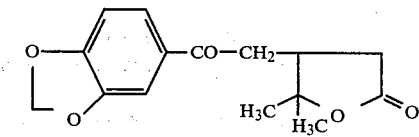

107 g of aluminum chloride were initially introduced into 400 ml of methylene chloride, and 76 g of 4,4-dimethyl-3-chlorocarbonylmethyl-γ-butyrolactone, dissolved in 100 ml of methylene chloride, were added dropwise at −5° to 0° C. 55 g of benzodioxole in 50 ml of methylene chloride were then added dropwise at 0°–10° C. Thereafter, the mixture was allowed to come to room temperature and was subsequently stirred for a further 4 hours. After pouring the batch into 1 liter of ice-water, the organic phase was separated off and washed until neutral. After drying and distilling off the solvent, 4,4-dimethyl-3-(3',4'-methylenedioxyphenacyl)-γ-butyrolactone was obtained.

EXAMPLE 18 (Process 18)

172 g of 4,4-dimethyl-3-carboxymethyl-γ-butyrolactone were mixed with 600 ml of thionyl chloride and the mixture was heated to 80° C. for 1 hour. Excess thionyl chloride was then distilled off under normal pressure, the last residues under a waterpump vacuum. The residue consisted of 4,4-dimethyl-3-chlorocarbonylmethyl-γ-butyrolactone ($n_D^{20}$=1.484) and could be used directly for process 16. However, it could also be purified still further by distillation; boiling point: 130°-140° C./0.3 mbar (in the case of relatively large amounts, the product must be distilled using a thin film evaporator). The pure acid chloride was solid. Melting point: 64° C.

EXAMPLE 19

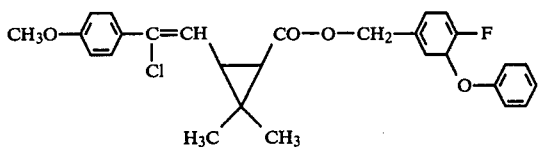

4.4 g (0.02 mol) of 3-phenoxy-4-fluoro-benzyl alcohol and 7.1 g (0.02 mol) of 2,2-dimethyl-3-(2-chloro-2-(4-methoxy-phenyl)-vinyl)-cyclopropanecarboxylic acid chloride were dissolved in 100 ml of anhydrous toluene, and 2.5 g of pyridine, dissolved in 50 ml of anhydrous toluene, were added dropwise at 20°–25° C., whilst stirring. Stirring was then continued at 25°–35° C. for 3 hours. The reaction mixture was poured into 150 ml of water, to which 10 ml of concentrated hydrochloric acid were added, and the organic phase was separated off and washed again with 100 ml of water. The toluene phase was then dried over sodium sulphate and the solvent was distilled off under a water-pump vacuum. Last solvent residues were removed by brief incipient distillation at a bath temperature of 60° C./1 Hg. 8.1 g (84.5% of theory) of 2,2-dimethyl-3-(2-chloro-2-(4-methoxy-phenyl)-vinyl)-cyclopropanecarboxylic acid 4-fluoro-3-phenoxy-benzyl ester were obtained.

The pesticidal activity of the compounds of this invention is illustrated by the following example:

EXAMPLE 20

Phaedon larvae test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were treated by being dipped into the preparation of the active compound and were infested with mustard bettle larvae (*Phaedon cochleariae*), as long as the leaves were still wet.

After the specified periods of time, the degree of destruction was determined in %: 100% meant that all of the beetle larvae had been killed whereas 0% meant that none of the bettle larvae had been killed.

In this test, for example, the following compound showed high activity.

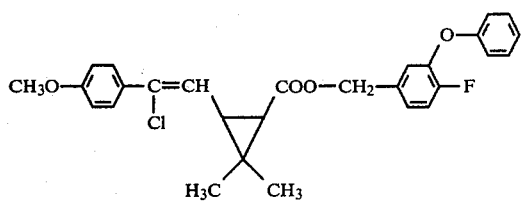

It will be appreciated that the instant specification and examples are set forth by way of illustration and not limitation, and that various modifications and changes may be made without departing from the spirit and scope of the present invention.

We claim:

1. A compound of the formula

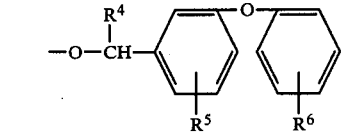

in which
R is $C_{1-4}$-alkyl or, $$-O-CH \begin{array}{c} R^4 \\ | \end{array} \text{(aryl)}-O-\text{(aryl)}$$

with $R^5$ and $R^6$ on the rings $R^4$ is hydrogen, cyano or ethynyl,
$R^5$ and $R^6$ is hydrogen or fluorine,
$R^1$ is alkoxy or alkylthio, either of which may be optionally substituted by halogen,
$R^2$ is hydrogen or alkoxy, or
$R^1$ and $R^2$ together are optionally halogen-substituted alkylenedioxy,
$R^3$ is hydrogen or chlorine, and
Hal is chlorine or bromine.

* * * * *

UNITED STATES PATENT AND TRADEMARK OFFICE
CERTIFICATE OF CORRECTION

PATENT NO. : 4,327,025
DATED : April 27, 1982
INVENTOR(S) : Manfred Jautelat, et al It is certified that error appears in the above-identified patent and that said Letters Patent are hereby corrected as shown below:

| | |
|---|---|
| Col. 5, line 65 | In structural formula delete "$H_3C-Cl$ <br>       $\|$ <br>      $CH_3$" and insert <br> --$H_3C-\underset{\underset{CH_3}{\|}}{C}-Cl$-- |
| Col. 8, lines 33 and 34 | Insert space between "cyanobenzl" and "alcohol" |
| Col. 11, line 18 | Delete "attached" and insert --attacked-- |
| Col. 12, line 8 | Delete "attached" and insert --attacked-- |
| Col. 12, line 35 | 1st structural formula dash is through C. Should read -CH=C |
| Col. 13, line 18 | Delete "(C)" and insert --(c)--. |
| Col. 13, line 34 | Beginning of 2nd line of formula delete "$CH_2O$" and insert --$CH_3O$-- |
| Col. 14, line 21 | Delete "alkyl" and insert --allyl--. |
| Col. 14, line 39 | After "sodium hydroxide" insert --potassium hydroxide--. |
| Col. 16, line 24 | Delete "$\alpha$" and insert --o--. |

UNITED STATES PATENT AND TRADEMARK OFFICE
CERTIFICATE OF CORRECTION

PATENT NO. : 4,327,025
DATED : April 27, 1982
INVENTOR(S) : Manfred Jautelat, et al It is certified that error appears in the above-identified patent and that said Letters Patent are hereby corrected as shown below:

Col. 16, line 33    Delete "customarily" and insert --customary--.
Col. 21, line 46    Delete "or" and insert --for--.
Col. 31, line  1    Lines inside F structure are wrong. It should read:

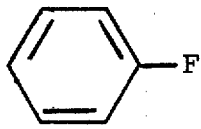

Col. 31, line 25    Insert --mm-- after "C/1".

Signed and Sealed this

Sixth Day of July 1982

[SEAL]

Attest:

Attesting Officer

GERALD J. MOSSINGHOFF

Commissioner of Patents and Trademarks